United States Patent [19]

Butler et al.

[11] Patent Number: 5,483,963
[45] Date of Patent: Jan. 16, 1996

[54] TWO DIMENSIONAL TRANSDUCER INTEGRATED CIRCUIT

[75] Inventors: Neal R. Butler, Acton, Mass.; Marvin E. Lasser, Potomac, Md.

[73] Assignee: Loral Infrared & Imaging Systems, Inc., Lexington, Mass.

[21] Appl. No.: 278,799

[22] Filed: Jul. 22, 1994

[51] Int. Cl.⁶ .................................................. A61B 8/00
[52] U.S. Cl. ................................. 128/661.01; 73/641
[58] Field of Search ................... 128/660.01, 660.08, 128/661.01, 662.03; 73/641, 642, 607; 367/7

[56] References Cited

U.S. PATENT DOCUMENTS

| | | |
|---|---|---|
| 4,224,829 | 9/1980 | Kawabuchi et al. . |
| 4,434,662 | 3/1984 | Green ........................................ 73/641 |
| 5,119,342 | 6/1992 | Harrison, Jr. et al. . |
| 5,121,361 | 6/1992 | Harrison, Jr. et al. . |
| 5,140,558 | 8/1992 | Harrison, Jr. et al. . |
| 5,381,795 | 1/1995 | Nordgren et al. .................. 128/662.03 |

*Primary Examiner*—George Manuel
*Attorney, Agent, or Firm*—Leone & Moffa

[57] ABSTRACT

A data acquisition and display apparatus for an ultrasonic camera includes an ultrasonic scanning head for scanning an ultrasonic field of view in two dimensions. A timing and digitizing apparatus for digitizing ultrasonic signals from the ultrasonic scan head has a digitized output. An interface is coupled between the timing and digitizing apparatus and a graphics engine and first and second digital signal processors. A graphics processor is coupled to the graphics data line. The system also includes an image processor and computer controller which controls the graphics and digital signal processors.

19 Claims, 7 Drawing Sheets

TWO DIMENSIONAL TRANSDUCER INTEGRATED CIRCUIT

The invention relates to a signal processing integrated circuit for an ultrasound imaging array and, more particularly, to a signal processing integrated circuit for an ultrasound imaging array formed of a two dimensional array of ultrasound transducers.

BACKGROUND OF THE INVENTION

Ultrasonic sensors have been used for many years in a wide range of applications, particularly medical imaging. Sensors manufactured as single elements and linear arrays, are often combined with some kind of scanning system to obtain additional data. The prior art shows some limited two dimensional arrays, but none incorporate a completely filled, two dimensional array of transducers.

Medical imaging technologies include B-scan ultrasound, MR imaging, nuclear medicine, CT imaging and limited C-scan techniques. The state of the art is discussed briefly below.

Convention B-Scan Ultrasound

The use of electronically steered linear and sector arrays for 2-dimensional cross sectional imaging is now well established. Such approaches require many pulse-echo interrogations to produce an image. The transducer must be moved in the out-of-plane direction to sweep volumes of tissue. Only in experimental models is the out-of-plane direction swept automatically using mechanical or electronic (2-D phase array) techniques. This requires a relatively slow build up of sequential two dimensional (2-D) sections with loss of temporal resolution. Cardiac pulse information is typically lost. More commonly, the sonographer sweeps the tissue in different orientations, and mentally reconstructs a model of organs, dimensions, and structures. Thus, conventional B-scan ultrasound is not well suited for imaging tortuous vasculature, irregular tumors and lesions, and other important structures and interfaces which are difficult to interpret as a sequence of 2-D slices. In contrast, C-scan imaging, as employed by the present invention, has depth time gating and interrogates a volume in one pulse-echo sequence. The result is a remarkable speed improvement that makes the assessment of three dimensional (3-D) structures more direct with less dependence on the scanning sonographer.

MR Imaging

Magnetic resonance (MR) imaging is capable of high quality 2-D cross sectional imaging, sequences of 2-D images, and new types of 3-D imaging for tissue and blood flow. However, MR scanners are high cost, not portable, not widely available and do not provide real time images. Furthermore, MR magnets restrict direct intervention, use of certain metals and wires, and also present a danger where metal fragments may be found. In contrast, inexpensive and real time C-scan ultrasound volume interrogation, as employed in the present invention, may provide advantages over MR imaging for many indications.

Nuclear Medicine

Renal nuclear scans are currently used to assess perfusion and activity of the kidneys. The procedures are slow, expensive, and require radioactive labeled agents. In comparison, the present invention employs C-scan imaging of kidneys that may produce real-time, dynamic imaging of the 3-D renal structure with none of the disadvantages of renal nuclear scans.

CT Imaging

CT imaging can produce sequences of 2-D cross sectional images of the body. However, CT imaging uses ionizing radiation which must be limited. Thus regular follow-up studies are restricted. CT equipment is generally expensive, not portable, and not accessible in many parts of the world. In contrast, the present invention's use of C-scan volume imaging with ultrasound may provide a substantial advantage over CT in imaging the liver, kidney, abdomen, and small parts of the body.

C-Scan

C-scan approaches include Kretztechnik in Austria and Tomtec in Germany. They have developed 3-D systems which rely on mechanical scan techniques. Mechanical scanning is slower, more complicated and far less versatile than the method for electronically scanning a 3-D image as taught in the present invention. Duke University has been credited with developing one of the first matrix arrays (nominally 20×20 and 32×32) for three dimensional imaging. However, the initial design was limited to operation below 2.3 MHz and the transmit/receive function was limited to only 32 elements in the array. In contrast to these previous efforts, by application of novel sensor design and the application of low noise analog and digital VLSI circuitry, the applicants have already demonstrated a fully active 64×42 array prototype, and both the higher frequencies and resolution needed for true 3-D medical ultrasound are realizable.

Finally, it should be noted that the equipment cost, patient preparation time, scan time, and ease of use are likely to be order(s) or magnitude better for C-scan technology than for nuclear imaging, MRI, and CT.

Application In Trauma Care

Important clinical situations, for both acute trauma and chronic care, may benefit from widespread use of inexpensive, real time C-scan imaging of 3-D volumes.

Inexpensive, portable, C-scan imaging may make a major impact in the early assessment of acute injuries. The volume scanning ability of C-scan imaging is ideal for identifying and measuring the extent and location of hemorrhage in the abdominal regions. Also, the hepatic and renal architecture, and blood flow with the addition of Doppler processing, may be readily evaluated in a way that, compared to B-scan imaging, may advantageously be less operator dependent and more robust for evaluation of 3-dimensional morphology. C-scan volume imaging is ideally suited for detection of foreign object fragments in the abdomen, the extremities, and the eye. In addition, guided biopsy is best performed under C-scan volume imaging which is ideally suited for detection of foreign objects such as metal, glass, and plastic fragments in the abdomen, the extremities, and the eye. In addition, guided biopsy is best performed under C-scan volume imaging since the 3-dimensional task of localization and visualization is more difficult to undertake using 2-dimensional imaging with conventional B-scan imaging.

A further area of application is preliminary estimation of cardiac wall motion. For example, acute myocardial infarcts can produce abnormal wall motion which is easily detectable with C-scan imaging. With Doppler processing, C-scan volume imaging can rapidly assess blood flow in the aortic arch, descending aorta, abdominal aorta, renal arteries, femoral artery, carotid artery, hepatic vein, inferior vena cava, and other vitally important vessels. Since important bifurcations and abnormalities are 3-dimensional structures, the volume imaging capability of C-scan imaging should provide greater diagnostic confidence with less operator independence.

Inexpensive, real-time C-scan imaging could be widely used in the field for assessment of acute injuries. This technology could bridge the large gap between taking vital signs and basic observations in the field, and taking CAT scans back in the hospital. With C-scan technology brought to the field, the ability to assess deep tissues is brought forward in time, enabling earlier assessment and intervention.

Application In Chronic Care

Guided Surgery and Biopsy

The removal of foreign objects in deep tissue, and the biopsy of lesions and tumors is increasingly guided by real time B-scan ultrasound. However, the nature of the 2-D cross section confounds many attempts to image a very thin needle or trocar. Unless the needle aligns closely with the 2-D imaging plane, only a narrow cross section will appear. This situation requires 3-D imaging to visualize both the target object and the biopsy needle. C-scan imaging can provide this needed 3-D orientation to assure that the lesion or foreign objects are properly targeted.

Renal Perfusion

A variety of acute trauma and chronic conditions, and other circumstances such as transplant rejection, can compromise renal perfusion with life threatening results. Conventional B-scan assessment of renal perfusion with color Doppler is hindered by the 3-D architecture of the renal perfusion which requires multiple 2-D cross section evaluations. If an ultrasound contrast agent is used to enhance blood flow detection, the resulting short washout curve is difficult to assess on B-scan as different 2-D cross sections are imaged. However, real-time C-scan volume imaging may capture the complete spatial and temporal evolution of an echogenic contrast agent into the kidney, providing a major leap in the diagnostic efficacy of ultrasound.

Carotid Artery Assessment

The carotid arteries provide blood to the brain, but can be compromised by acute incidents and chronic conditions. Mapping the 3-D architecture of the carotid bifunction, with a careful assessment of the internal lumen, is time consuming and very operator dependent for conventional B-scan imaging. However, C-scan volume interrogation should produce rapid and complete visualization of the carotid bifunction. In this case, the addition of contrast agents and/or Doppler capabilities with true C-scan volume imaging, may revolutionize the diagnostic impact of ultrasound in terms of speed, cost, and confidence.

Liver Metastases

In cancer therapy, it is vitally important to image and measure the growth or reduction of tumors within the liver. Conventional B-scan ultrasound can accomplish this only with operator intervention to choose the "correct" 2-D cross section that will be used to define the "diameter" of the tumor. C-scan volume rendering is required to produce accurate, unbiased, and less operator dependent measurements of 3-D tumors within the normal liver parenchyma, and in other soft tissues such as the thyroid and breast.

SUMMARY OF THE INVENTION

A data acquisition and display apparatus for an ultrasonic camera includes an ultrasonic scanning head for scanning an ultrasonic field of view in two dimensions. A timing and digitizing apparatus for digitizing ultrasonic signals from the ultrasonic scan head has a digitized output. An interface is coupled between the timing and digitizing apparatus and a graphics engine and first and second digital signal processors. A graphics processor is coupled to the graphics data line. The system also includes an image processor and computer controller which controls the graphics and digital signal processors.

In one aspect of the invention, an ultrasonic input circuit is employed comprising a transducer with a diode connected across a bias voltage. The bias voltage is connected to one terminal of the transducer and the diode is connected to a second terminal of the transducer. A current source is connected between the bias voltage and an emitter of a preamplifier wherein a gate of the preamplifier is connected to the second terminal of the transducer. A reference voltage supply is connected to a drain of the preamplifier, wherein the preamplifier is switched under control of a digital controller wherein the digital controller can sample at least one time period of the output of the preamplifier source into at least one integration capacitor.

In another aspect of the invention, the ultrasonic input circuit comprises a shift register for controlling a plurality of storage elements for individually sampling the output of the preamplifier source at periodic intervals.

BRIEF DESCRIPTION OF THE DRAWINGS

To illustrate this invention, a preferred embodiment will be described herein with reference to the accompanying drawings.

DETAILED DESCRIPTION OF THE PREFERRED EMBODIMENT

Figure 1:
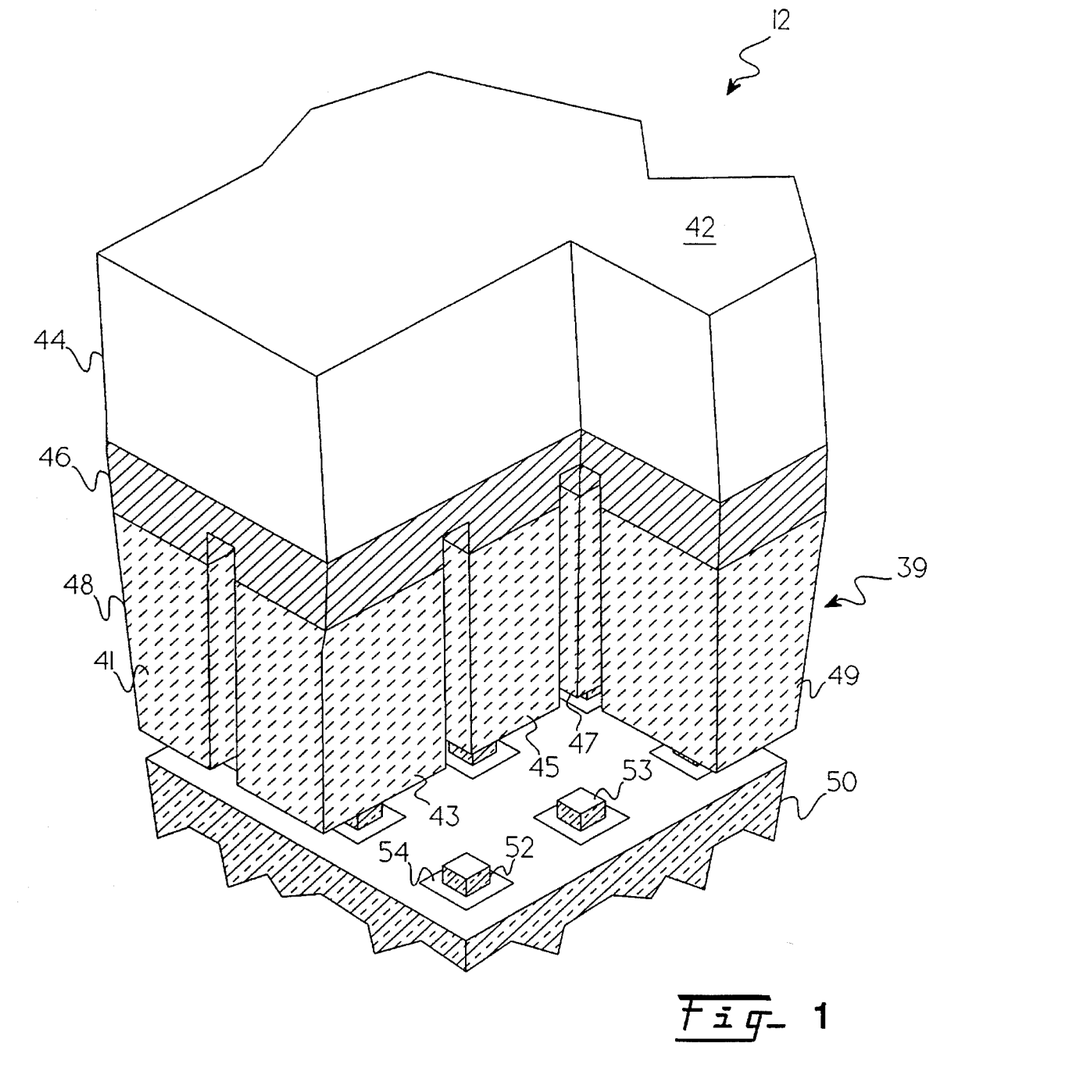
FIG. 1 shows an isometric drawing of a portion of the ultrasonic transducer array and an integrated signal processor.

Refer now to FIG. 1. FIG. 1 shows the acoustic array 12 of the invention embodied as part of a 128×128 array. Each ceramic "piezel" 41, 43, 45, 47 and 49 is comprised of ultrasonic transduction material and is bonded using indium bumps similar to indium bumps 52 and 53, to CMOS VLSI integrated circuit 54. In one preferred embodiment, the piezel is 150 µm wide.

Figure 5:
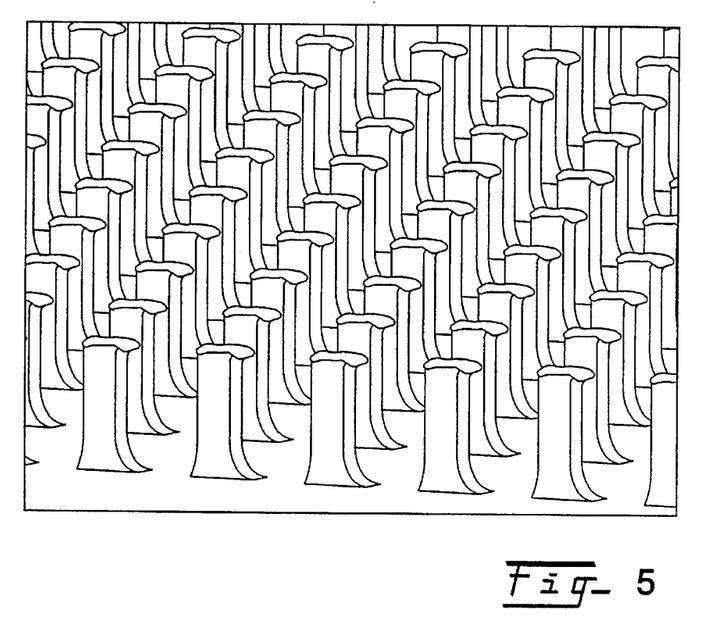
FIG. 5 shows a scanning electro micro-graph of the ultrasound transducer array of the invention.

The acoustic array 12 was assembled by bump bonding of a reticulated array of PZT detectors to an existing integrated circuit originally designed for an uncooled pyroelectric focal plane array. Each detector was separated by a half wavelength at approximately 5 MHz ultrasound, and was designed with a thickness of 15 mils to maximize signal-to-noise properties. FIG. 5 shows a scanning electron microscope photograph of the array 12, showing the saw cut reticulation between the elements that provides the isolation required.

Ultrasonic imagery is a powerful, noninvasive diagnostic tool. In practice, its usefulness has been limited due the small size of available transducer arrays. The small array size forces tradeoffs between resolution and image acquisition time. A nonscanned linear array can display near real time imagery but with a large penalty in resolution in one dimension, yielding imagery which is difficult to interpret.

The principal reason for the limited size of transducer arrays is the difficulty of fabricating the associated electronics. Modern integrated circuit technology makes it possible to fabricate this circuitry 54 in the area occupied by one element in the two dimensional array of transducers 12. Known hybridizing technology developed for arrays of infrared detectors may then advantageously be used to connect the transducer array to the electronics integrated circuit 54.

In one example embodiment, the ultrasonic scan head 61 comprises a 128×128 element two dimensional array with in phase and quadrature detectors and preamplifiers. The benefits of this architecture include high resolution in three dimensions, two-dimensional C-scan imagery from single pulses, and rapid (i.e. less than 1 second) acquisition of three-dimensional imagery. The processing electronics include:

Dual sets of in phase and quadrature detectors for pulsed Doppler measurements;

Receive phase shifters for a wider range of beam steering;

Transmit phase shifters for transmit beam forming; and

High bandwidth readouts for real time acquisition of three dimensional and pulsed Doppler imagery.

FIG. 1 shows the individual piezels 41, 43, 45, 47 and 49 hybridized onto the silicon Read Out IC (ROIC) 54. The saw cut reticulation has been made completely through the ceramic 48 and part way into the first matching layer 46. By cutting all the way through the PZT layer 48, electrical and mechanical crosstalk can be virtually eliminated thereby improving the resolution of the directed beam, as well as the received data. Furthermore, by using air in between the piezels 41, 43, 45, 47 and 49 as an acoustical insulator, acoustic crosstalk can be reduced significantly as well.

Acoustic array 12 optionally comprises a protective seal and cover 42 with an outer matching layer 44 and a conductive inner matching layer 46. By matching the acoustic impedance of the ceramic detector 39 with that of body tissue through the use of matching layers 44 and 46 transducer sensitivity increases sharply. The outer matching layer 44 may comprise an acoustic material or composite material having an acoustic impedance suitable for coupling of energy to the transducer elements. Plastic or tungsten-loaded araldite has been used to make quarter wave matching layers. See *Diagnostic Ultrasonics: Principles and Use of Instruments* by W. M. McDicken (1991). The inner matching layer 46 may comprise a thinner layer of a conductor, such as gold, for example for contact to the PZT layer 48.

| Type and Mixture |
| --- |
| Tungsten-Epoxy |
| Glass (Light Borosilicate) |
| Al-Epoxy |
| Al—Mg-Epoxy |
| Melopas |
| Glassbeads and Epoxy |
| Glassbeads and Epoxy |
| (XP24136) |
| Lucite |
| (Polymethylmethacryiate) |
| Polysulfone |
| Polycarbonate |
| (Lexan) |
| Epoxy 1 |
| Polystyrene |
| (Cross Linked) |
| TPX (methylplaten) |
| Water |
| PTV830 |

Figure 2:
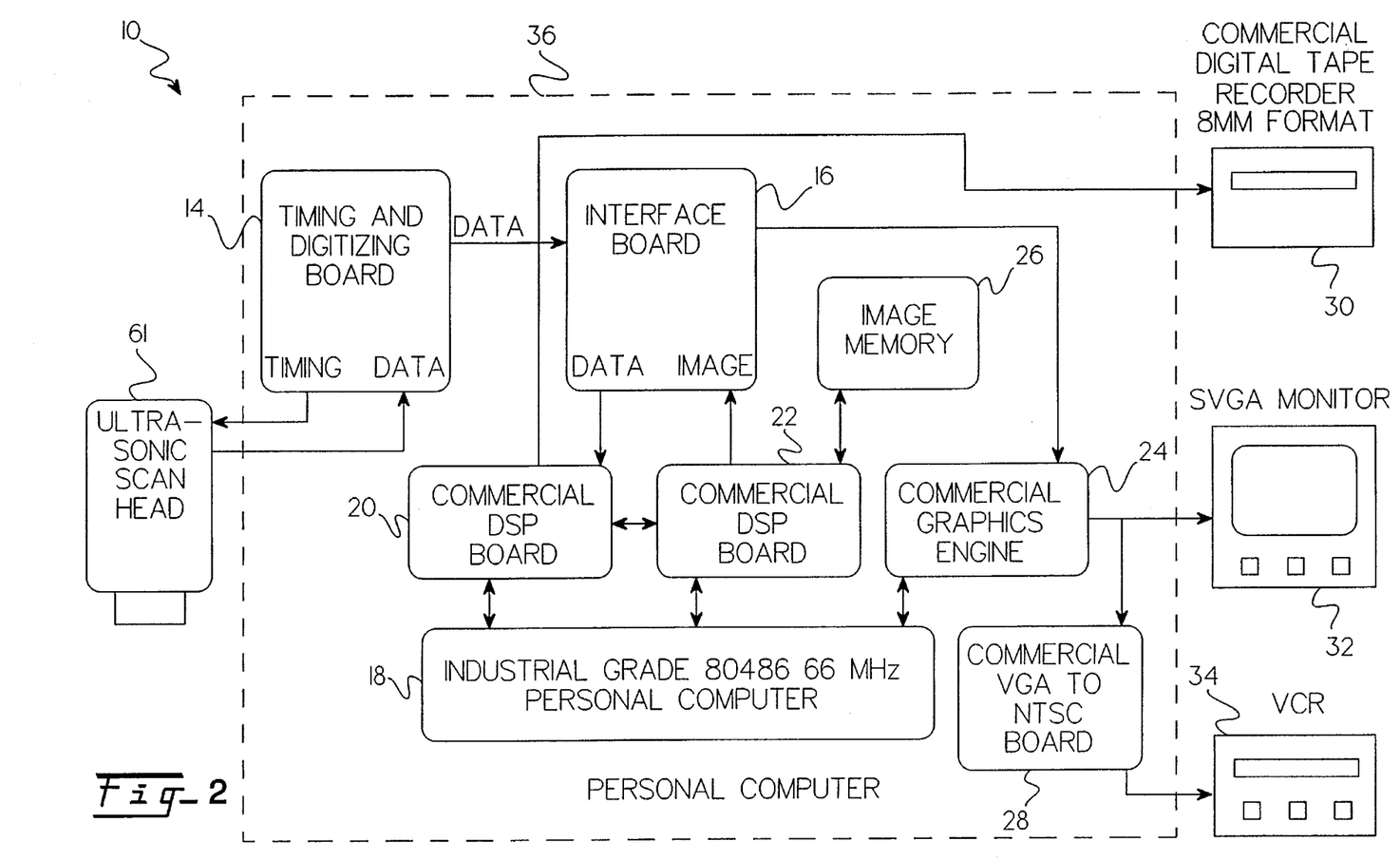
FIG. 2 shows a schematic diagram of the data acquisition and display system of the invention.

Now referring to FIG. 2, the ultrasonic array 12 used in a data acquisition and display system 10 as employed in one embodizent of the invention is shown. The data acquisition system 36 is attached to ultrasonic scan head 61 and to commercial digital tape recorder 30, SVGA monitor 32 and VCR 34.

Data acquisition system 36 comprises a timing and digitizing board 14 which provides data to an interface board 16. The interface board 16 sends data to a commercial digital signal processor (DSP) board 20 which may comprise a Texas Instruments model TMS320-C30 digital signal processor. The interface board 16 also acquires image data from a second commercial DSP board 22 which may also comprise a model TMS320-C30. The digital signal processors 20 and 22 communicate with each other in a well known manner. An industrial grade personal computer 18 is used to control the two DSP boards and a commercial graphics engine 24 which, in one example embodiment, may be a model TMS34020, also made by Texas Instruments. The interface board 16 sends data to the commercial graphics engine 24. The commercial DSP 20 also sends data to a tape recorder 30. The commercial graphics engine 24 sends data to the SVGA monitor 32 and commercial VGA to NTSC board 28 which sends data to a video cassette recorder 34. The ultrasonic scan head receives timing data from the timing board 14 and sends data to the digitizing board 14. This data is then sent to the interface board 16.

In one example embodiment, the computer 18 programs the transducer IC 54 contained in the ultrasonic scan head 61 for the desired mode of operation and acquires data from the 16,384 array elements. Multiple frames of data may be combined to form a three dimensional image data base, which may then be displayed using operator controls.

Figure 3:
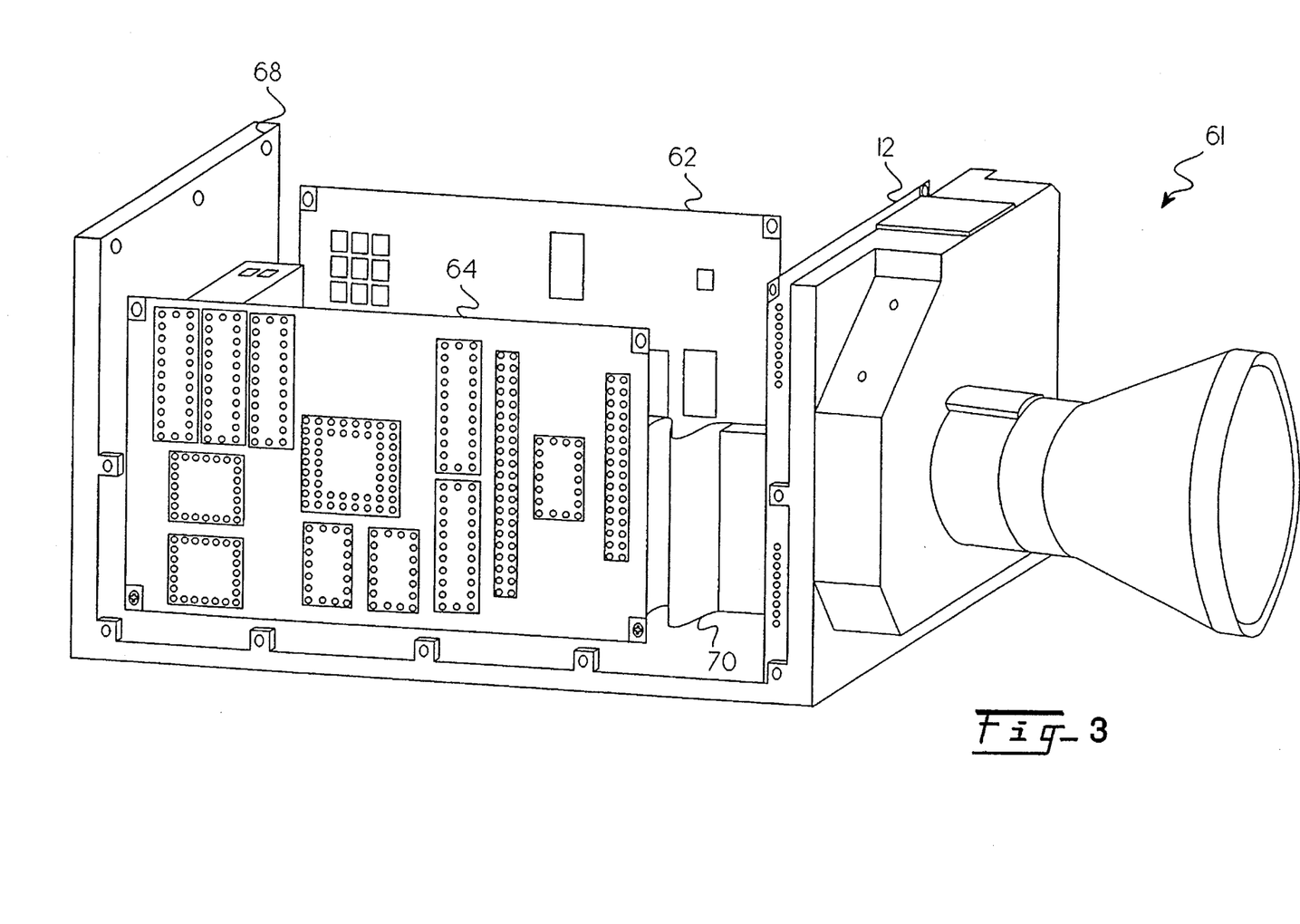
FIG. 3 shows a picture of the ultrasonic imaging camera of the invention.

Refer now to FIG. 3, the ultrasonic focal plane array 12, with its integral acoustic matching layers 42, 44 and 46 is mounted along with I/O electronics 62, 64 and connector 70 in a plastic housing 68. The sensor array interface electronics 54 embedded within the scan head assembly 61 contains the necessary bias, timing and buffer electronics to drive the array 12 as well as transmit image data back to the data acquisition system 36 over a slender 10 foot cable. Thus, the apparatus of the invention allows the use of a slender cable which is a significant advantage over the current state of the art.

Figure 4A:
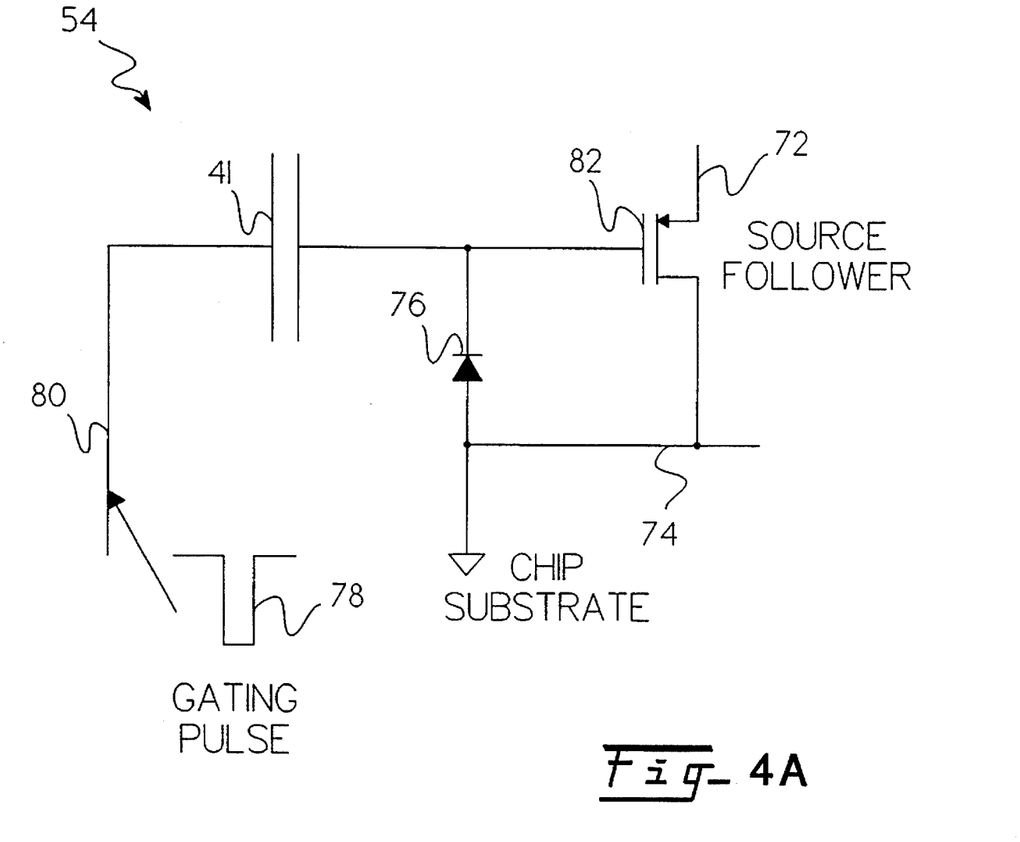
FIGS. 4A and 4B show an electronic circuit diagram of the processing electronics of the invention.

Now refer to FIG. 4A; FIG. 4A shows an input circuit 54 for the sensor array 12. The piezel transducer 41 comprises an ideal capacitor having a gating input pulse 78 on line 80. The chip substrate 74 is isolated by diode 76. The transducer 41 drives a source follower 82 which provides an input 72 to multiplexer circuitry. The source follower 82 provides the detected signal for piezel 41. Each piezel is provided with a similar input circuit 54.

Figure 4B:
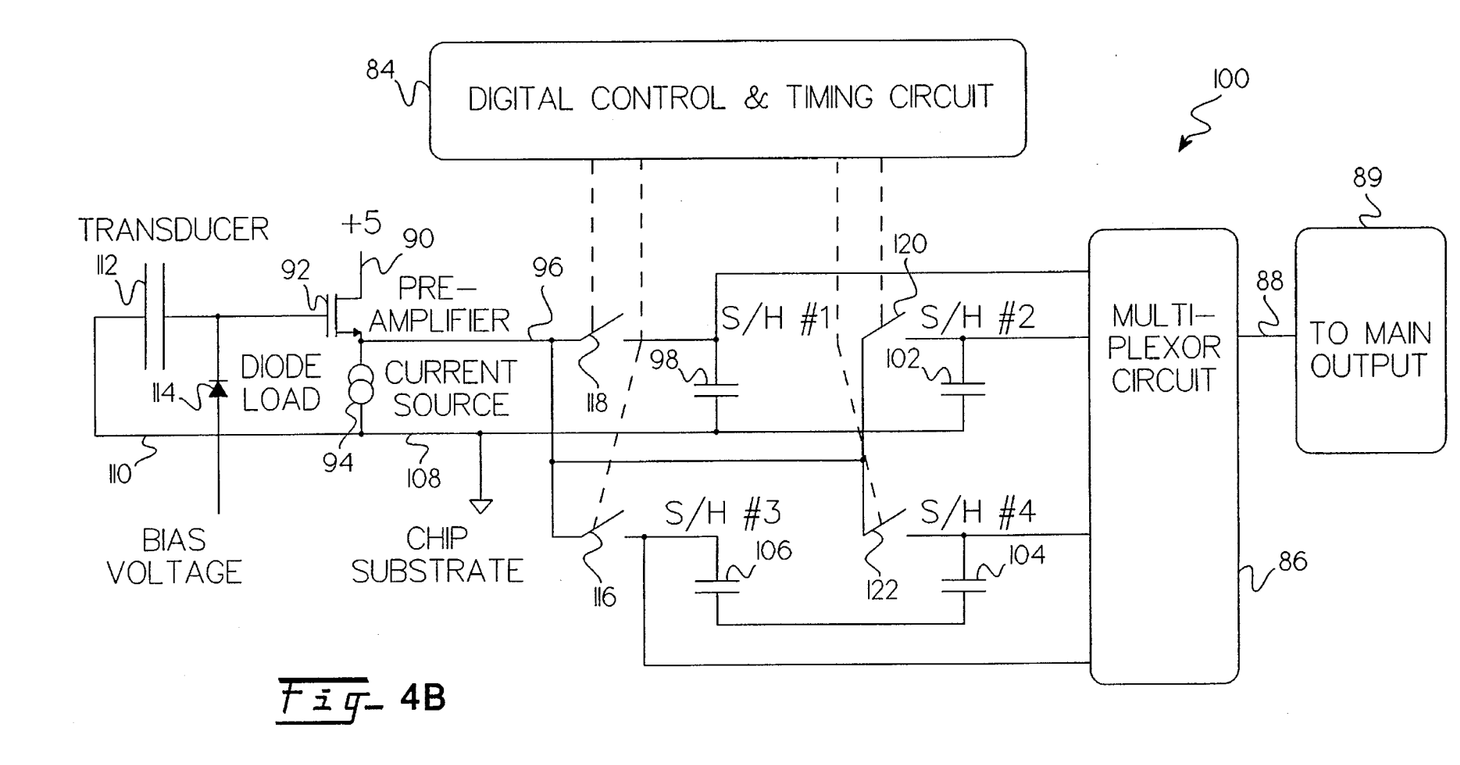

Now refer to FIG. 4B; FIG. 4B shows an example of an alternate input circuit 100 for the ultrasonic transducer array 12. Each piezel 112 has an associated input circuit embodied in the semiconductor substrate 50. The alternate input circuit is digitally controlled and timed and designed to provide a multiplexer circuit 86 with inputs from first through fourth sample and hold circuits. The circuit 100 has a preamplifier 92 which is biased with about five volts by line 90. A current source 94 provides line 96 with a signal which is also coupled to the output of the preamplifier 92. The preamplifier amplifies the signal from the piezel 112. A bias voltage 110 is provided to the transducer. A load diode 114 is connected across the output of the piezel 112 and the bias voltage 110. Integrated circuit chip substrate 108 is connected to one side of the current source 94. Sample and hold capacitors 98, 102, 104 and 106 sample and hold signals for various timing periods of the circuit when switches 116, 118, 120 and 122 are closed in response to a control signal received from digital controller 84.

Preamplifier 92 buffers the piezel 112 impedance to drive the four sample and hold switches. The load diode 114 controls the DC voltage at the preamplifier 92 input. The control and timing circuits operate the sample and holds preferably consecutively. Multiplexer 86 is provided to multiplex the output of each of the 128×128 piezels to a multiplexed output 88.

In one preferred embodiment of the invention, multiple sample and hold circuits are provided to allow for higher overall data rates. In an alternate embodiment, the sample and hold circuits may be preceded by a cross-correlator circuit for pulse stretching and compression to reduce transmit power requirements.

A cross-correlator circuit multiplies two different signals together and averages the result. One of the signals is varied in time with respect to the other, and the process is repeated. This is a very general type of circuit. The S/H circuits shown in FIG. 4B meet this definition, since the transducer signal is multiplied by another signal which is usually zero except for a small time interval. The timing of the reference signal is varied over some range and the results are recorded for further processing. The only difference involved in a more general cross-correlator is the ability to have a different kind of reference signal, in particular a digital pseudo random sequence. This is a standard technique for detecting the presence of a long, complicated signal in the presence of noise. In this application, this approach has the advantage that the output of the correlator tends to be near zero except when the reference signal and the received signal coincide in time. The time resolution may be much smaller than the length of the signal. This allows for the signal energy to be spread out in time for a lower peak signal power for the same overall signal to noise ratio.

With an integrated circuit, fabricating multiple cross-correlators for each transducer may be only a little more complicated than the sample and hold circuits. The equivalent amount of computation done can be quite large, since there may be many thousands of these cross-correlators operating in parallel.

The input circuit 100 detects the pulse from each array element and stores the result in analog form until it can be read out by the multiplexing circuitry at a rate slow enough for external circuitry to digitize.

In the instant example, a digital control and timing circuit 84 operates the first through fourth sample and hold circuits. The digital control and timing circuit 84 may comprise, for example, a shift register which clocks a control bit through sequentially to operate each sample and hold circuit in sequence. For example, if the ultrasonic scan head 61 is operating at a 5 MHz rate, the array must be sampled at 100 nanosecond intervals in order to satisfy the Nyquist sampling criteria. Each of the sample and hold capacitors 98, 102, 104 and 106 may then be accessed by the multiplexer circuit 86 for output to downstream electronics 89 whenever the computer interface is ready to accept them. While an input circuit has been shown for a single transducer, it will be understood that all transducers on the array may be sampled simultaneously and that the circuit shown in FIG. 4B is duplicated for each transducer in the two dimensional array. It will also be understood that the number of sample and hold circuits employed may vary depending upon the application and speed of the other down stream processing elements.

Devices available with a standard CMOS integrated circuit process are well matched to the characteristics of PZT transducers, allowing for detection of very low level signals with excellent signal-to-noise ratios. In some embodiments of the invention, dual mixers are contemplated to double the data rate by allowing detection of in phase and quadrature components of each pulse.

In an alternate embodiment of the invention, it is contemplated that quad mixers may advantageously allow for Doppler imaging by measuring the phase shift between two pulses spaced closer together than the normal electronics frame time.

Receive phase shifters allow beam steering for receive. This allows the function of an acoustic lens to be performed in software, for much more flexible imaging and a smaller transducer. Both the focal length and overall angle of the array could be changed. The phase shifters can be readily implemented in CMOS.

In an alternative embodiment of the invention, the input circuit may comprise multiple cross-correlators followed by sample-and-hold circuits. This option includes all the mixer options as special cases. It can also be used to demodulate special transmit code sequences and reduce the external processing load. The cross-correlator consists of a modulator which reverses the sign of the transducer signal according to a digital signal and then averages the output. If the digital signal matches the transmitted signal, then the cross-correlator output is large, otherwise it is small. This is a standard technique in radar and sonar systems. The present invention is to include multiple correlator circuits, all operating in parallel, onto a single integrated circuit with the ultrasound transducers and preamplifiers.

Receive phase shifters insert a time delay into the received signal. When a complete image is to be generated by external processing, the value of the received signal at a wide range of delays is required. Therefore, the preferred method of receive phase shifting is simply to generate samples at intervals which satisfy the Nyquist criterion. Then the external processor selects those samples, or interpolates between actual samples, as needed for any given computation. Transmit phase shifters are not strictly necessary. The transmitter may simply transmit to the entire volume of interest at all times, with no steering of focusing.

Although ultrasound transmission from an integrated circuit will be difficult due to the high voltages normally used, there may be applications which can benefit from the ability to form an arbitrary beam shape. In addition, the use of pseudo random sequence coding or other similar techniques have the potential for dramatically reducing the required transmit power, making lower voltage operation feasible. In such a configuration, the transmit circuit generally requires adjustable phase shifting for each transducer. This can be obtained with an array of flip-flops, which can be switched in and out on a cell by cell basis. Thus, the delay from cell to cell can be individually adjusted in increments of one clock cycle. By using a programmable array of this sort, nearly any desired pattern can be obtained. Since the flip-flops represent true, digital, delays, any type of transmit sequence, such as a pseudo random sequence, can be used to form the beam.

Figure 7:
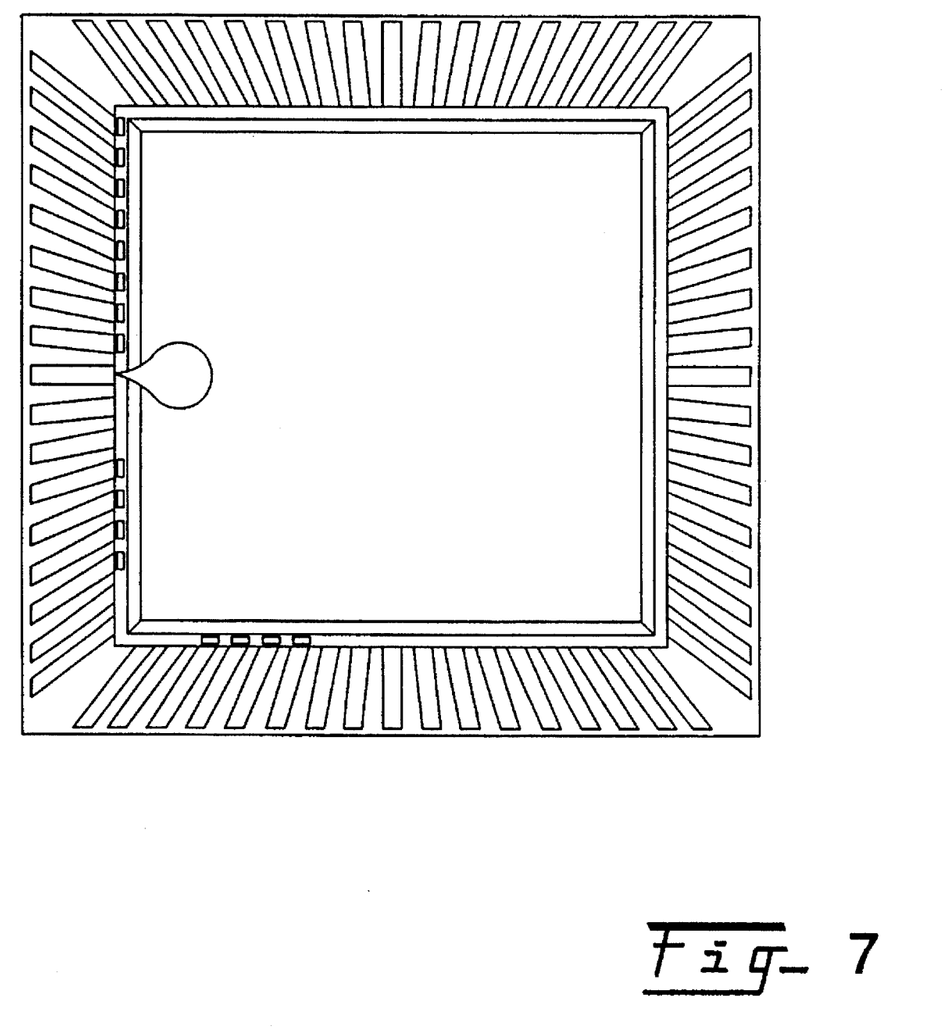
FIG. 7 shows a picture of a 64×42 array made in accordance with the present invention.

A limited prototype device consisting of a 42×64 array of PZT transducers mounted to an integrated circuit readout chip has been fabricated and demonstrated, as shown in FIG. 7. This device is the first in family of ultrasonic sensors which are dramatically different from all previous devices, because much of the essential electronics are contained within the sensor itself. Modern integrated circuit technology allows all of the essential signal processing functions to fit into an area equal to the area of a single element in the array. In addition to making two dimensional arrays feasible for the first time, the elimination of stray interconnect capacitance results in significant increases in the sensitivity of the transducer-electronics combination.

Figure 6:
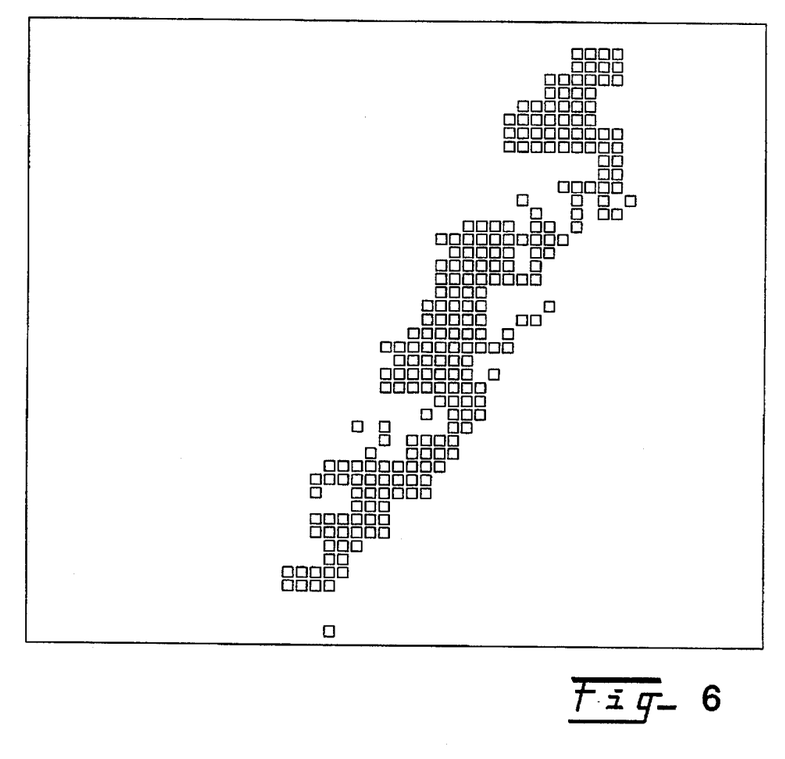
FIG. 6 shows an ultrasound image generated from the invention.

Modifications were made to existing IR camera timing electronics to incorporate a time gate capability and the ultrasound signal rectification as required for ultrasound imagery. Resolution of the time gate was chosen to be 1 μs. By moving this time gate in 0.5 μs increments a series of parallel image planes was generated, each on top of the other and separated by ~0.75 mm. The demonstration consisted of placing the source in a water tank and coupling the sensor array to the water through a thin rubber membrane. The focused line source was then driven with 5.0 volt, 5 Mhz, 1 μs pulses and swept in front of the 2-D ultrasonic array. The source was then held in a field location and the time gate incremented over a 32 μs range to demonstrate data collection in the third dimension. FIG. 6 shows an example of the image.

In one embodiment of the invention, a portable data acquisition and display system is used to operate the scan head 61 and present real time imagery to the operator. A commercial personal computer 18 with off-the-shelf backplane boards performs signal processing and image display functions. Features of the system include:

An 8 mm digital recorder 30 for saving digitized scan data for subsequent image analysis and image archiving;

An interactive menu driven user interface for control of the display 32 and scan head 61 as well as recording interfaces;

A Digital Signal processing board 20 for executing a fast fourier transform on the phase and quadrature image frames to generate an acoustic image without the use of an acoustic lens;

A Digital Signal processing board 22 capable of performing image display techniques such as reslicing, surface rendering and volume rendering; and A timing and digitization board 14 for operating the scan head 61 and converting the analog scan head output to digital form.

The data processing and recording electronics consists of an industrial grade PC Compatible computer 18 operating as a host to processing cards containing Digital Signal Processor (DSP) chips.

The timing and digitizing board 14 generates system timing signals needed to synchronize the scan head 61 with the Analog to Digital converters. After digitization, the sensor signals are transferred to an interface board 16. This interface board 16 buffers and formats the data for reading by the first of the DSP boards 20. The interface board 16 also takes processed image data from the second DSP board 22 and formats the image data for the graphics processor 24.

The described total system is based on current IR imager systems. In such systems, an interface board is required to suitably condition the signals and power supplies for the sensor IC. The interface board typically includes power supply filtering and regulation, analog buffers to transmit the high speed analog outputs from the IC down a cable to the remainder of the electronics, and such clock timing and control logic as needed to generate the master timing signals required by the sensor IC.

The timing and digitization board generates timing logic signals for the entire system, including the sensor and the DSP interfaces. It also includes the analog to digital converter which digitizes the sensor outputs. In one alternate embodiment of the invention a larger portion of these functions may be incorporated in the sensor in order to reduce the total system cost and improve performance. In particular, the ultrasound sensor may include the digitization function on the sensor IC.

The main function of the first DSP board 20 is to perform real time fast fourier transforms (FFT) on the digitized ultrasonic data. The second DSP board 22 will build a three-dimensional array in memory 26 of the FFT data and process this data to form images for display. The processing of images will allow for real time viewing of two dimensional slices anywhere within the three dimensional scene. Additional processing builds three dimensional maps of the edge boundaries of objects within the array to allow three dimensional viewing of regions or objects of interest.

The graphics processor 24 accepts image data in either two dimensional or three dimensional forms and may scale, rotate, assign colors or gray scales and format the image data in a graphical format for display on the high resolution color monitor 32. The graphics processor also may be used to merge computer text information such as menus for the operator to manipulate the image. Scaling, zooming, panning and image rotations are all features that the user could use to view the image. A VGA to NTSC circuit card 28 may advantageously provide a television format of the graphics image for recording on standard video tape. The 8 mm digital tape recorder 30 may be used to record the digital data in a computer readable form for analysis.

SIGNAL AND IMAGE PROCESSING

The image processing of the invention utilizes the unique features of the 2-D array 12 to address the problems of phase aberration and speckle noise. Both phenomenon have a considerable impact on the quality of imagery from current B-scan systems, but are amicable to solutions feasible in 3-D ultrasound.

The effects of intervening inhomogeneous tissue on image quality have been studied by various investigators. Because of the ionizing radiation involved in x-rays, sonography may be the imaging method of choice to be used in many routine examinations, if sonographic images provided adequate resolution. However, this resolution does not seem to be available from clinical scanners due to phase aberrations resulting from spatial variations in refractive index in intervening tissues.

In addition to the loss of resolution resulting from phase aberrations in the passage through tissue there is a loss of image quality due to speckle. For ultrasound, the image contains an imaginary phase component whose impact is of considerable practical importance. It is the physical counterpart in transform space of the phenomenon of interference between multiple overlapping point sources. In certain circumstances, e.g, holographic systems, this imaginary component may represent useful transfer of information through the imaging system. In conventional echographic systems, however, this phase information is lost in the process of detection, or rectification, of the signal. The principal effect of the phase component is to impose, on the image, a spatially pseudorandom and essentially meaningless amplitude modulation: in other words, a form of noise. The impact of this phenomenon, so called coherent radiation speckle, on imaging performance can be severe.

Phase Aberration Correction

In a phased array system, the electronic phase delays that are used for focusing and steering can also be used to compensate for phase aberrating tissue between the transducer and the region of interest (ROI). Such a correction should provide a more accurate image of the organs in the focal range. Previous investigators have investigated a technique by which phase delays can be modified in order to correct some of the detrimental effects of phase aberration. The invention uses a method called Coherent Adaptive Optical Techniques (COAT) which was developed for atmospheric turbulence correction of coherent light beams. A detector is placed in the focal plane at a target and the modulation intensity is sensed. Since the target is usually inside a body, the detector can be placed near the transmitter. Energy from the target is reflected into the detector and will have the same modulation in intensity as on the target. The resulting signal contains the information used to drive the average phase in the channel toward an intensity maximum. Control of the phase of the signal is a common technique in ultrasonic systems, the best example being the beam steering by varying the phase along the array.

Speckle Reduction

Because it does not have a one-to-one correspondence with scatterers in the object, speckle is sometimes thought to be an annoying artifact. However, as mentioned above, speckle reduces target detectability by reducing the useful spatial resolution. The amplitude of the speckle noise is inherently high just in the spatial frequency corresponding to the physically achievable spatial resolution. Resolution of this conflict is one of the central problems of echographic perception. Speckle fundamentally results from the coherent nature of the imaging procedure and thus, any technique to increase the signal-to-noise ratio must reduce the degree of coherence. The most straightforward method is to reduce or cancel the speckle effects visually. Since our imaging method provides a real-time image across a plane, the method just described will also be applicable for speckle reduction. Once the aberration corrections are made as described above, the phases of the multiple reflections are varied at a rate higher than a frame time (which is typically 1/30 s) so that over the frame period the coherence on the average is destroyed.

OPERATION

The two dimensional array 12 can be operated in the so-called "C-scan" mode wherein a complete two dimensional image can be formed from a single ultrasound pulse. A multitude of such images creates a three dimensional data base which can be readily manipulated by computer software to display the data in a variety of useful formats.

The invention utilizes circuits which are compatible with standard CMOS integrated circuit technology. Most of the phase shifting and beam forming strategies now used with linear arrays can not be really transferred. One technique which is compatible is the use of mixers or phase sensitive detectors. This technique is well known, but its advantages for integrated circuit implementations have not been previously recognized. A mixer can be implemented with only a few components on the IC, and its output can be stored on a small capacitor until time for readout. The receive beam forming function can be done using computations on the outputs of the mixers, which is well documented in the literature.

It is possible in principle to form both transmit and receive phased arrays with mixers. A possible alternate is the utilization of very long, specially coded pulses, together with matching correlation filters on the integrated circuit. A more conventional solution is to simply use a separate transmitter. The transmitter beam does not need to be controlled with much accuracy, so it could use very limited phase shifting, or even mechanical scanning.

Another embodiment for overcoming the integrated circuit voltage limitations includes a separate transducer for transmitting. This transducer may be designed to disperse the ultrasound energy uniformly throughout the volume to be imaged. Since the safety requirements are in terms of energy density (W/cm$^2$), rather than in terms of total power, there should be at most a minimal penalty in system sensitivity due to such a configuration.

It is also possible to overcome the transmit voltage limitation by applying a high voltage transmit pulse to the transducer electrode which is normally grounded. Then the integrated circuit holds the other electrode, on which the receive signal is sensed, to ground or some other constant voltage during the transmit pulse. The circuitry to do this will not need a high voltage rating, and can be designed to have minimal impact on the receive sensitivity. If all of the transducers were pulsed simultaneously, the ultrasound energy may not necessarily have a useful spatial distribution. By applying different transmit pulses to groups of transducers, a limited beam forming capability could be obtained without increasing the amount of electronics too much.

The piezoelectric transducers may be advantageously combined with the properties of PVDF (polyvinylidene fluoride) and copolymers incorporating PVDF. These materials have so far found limited application as ultrasound transducers due to their low dielectric constant, which makes them more susceptible to signal loss in stray interconnect capacitances. In addition, these materials show their best performance when backed by a solid material. The solid backing allows for a lower thickness transducer because it lowers the resonant frequency by approximately a factor of two.

The addition of a damping layer underneath the integrated circuit serves to minimize unwanted vibrational modes of the sensor. Together with a polymer transducer array, such a sensor provides a very low level of such unwanted responses.

Given the image formed by the sensor of the invention, it becomes practical to improve on the image by varying the phase front of the ultrasonic beam to reduce or eliminate aberration and speckle.

The sensor of the invention is able to display many more elements/second that can be achieved with conventional B-scan imagery by integrating over a number of frames in a short time period to improve the signal-to-noise. An available alternative is to work at a higher than normal frequency and to compensate for the associated loss in signal strength by again integrating over a number of pulsed frames. Working at the higher frequency will result in higher resolution.

The invention can be employed in a manner analogous to that of conventional X-ray imaging. It is passed through the body and produces an image representing the attenuation experienced in different paths. It may correlate with and complement the information obtained with X-rays. Multipath and scattered radiation can be removed by gating of the received signal.

With a 2-D ultrasonic array, ultrasound can be employed in a manner analogous to that of conventional X-ray imaging. It is passed through the body and produces an image representing the attenuation experienced in different paths. Such an approach could be correlated with and complement the information obtained with X-rays. The effects of soft tissue interfaces may provide information not available from X-rays. Also when compared to ultrasonic reflective imaging, radiation striking an interface at an angle may not be reflected back, but may show up on transmission.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A data acquisition and display apparatus for an ultrasonic camera comprising:
   (a) an ultrasonic scanning head means for scanning an ultrasonic field of view in two dimensions having an ultrasonic signal output for carrying an ultrasonic signal;
   (b) a timing and digitizing apparatus for digitizing the ultrasonic signal from the ultrasonic scanning head means having a digitized output, wherein the timing and digitizing apparatus is coupled to the ultrasonic signal output;
   (c) an interface means for interfacing digitized data to a graphics processing system, where the interface means is coupled at an input to the digitized output, wherein the interface means comprises a data line, an image data line and a graphics data line;
   (d) first digital signal processing means for processing data, the first digital signal processing means being coupled to the data line;
   (e) second digital signal processing means for processing data, the second digital signal processing means being coupled to the image data line for providing image data to the interface means, the second digital signal processing means also being in communication with the first digital signal processing means and sharing an image memory data line;
   (f) a graphics processing means for graphics processing image data, the graphics processing means being coupled to the graphics data line, and wherein the graphics processing means includes a graphics output;
   (g) an image memory means for storing image data, the image memory means being coupled to the image memory data line; and
   (h) a computer controller for controlling the graphics processing means, first digital signal processing means and second digital signal processing means, the computer controller sharing a first path with the graphics processing means, a second path with the first digital signal processing means and a second path with the second digital signal processing means.

2. The data acquisition and display apparatus of claim 1 further comprising a monitor means for viewing graphics data, the monitor means being coupled to the graphics output.

3. The data acquisition and display apparatus of claim 1 further comprising a means for converting data to a video format, the video format means being coupled to the graphics output.

4. The data acquisition and display apparatus of claim 1 wherein the ultrasonic scanning head means further comprises:
   (a) a plurality of ultrasonic input circuits, each ultrasonic input circuit comprising:
      (i) a transducer with a diode connected across a bias voltage, wherein the bias voltage is connected to one terminal of the transducer and the diode is connected to a second terminal of the transducer;
      (ii) a current source connected between the bias voltage and an emitter of a preamplifier wherein a gate of the preamplifier is connected to the second terminal of the transducer; and
      (iii) a reference voltage supply connected to a drain of the preamplifier, wherein the preamplifier is switched under control of a digital controller wherein the digital controller can sample at least one time period of an output of the preamplifier source into at least one integration capacitor.

5. The data acquisition and display apparatus of claim 4 wherein the first digital signal processing means includes a digital tape output, the data acquisition and display apparatus further comprising a digital storage means for storing data coupled to the digital tape output.

6. The data acquisition and display apparatus of claim 5 wherein the digital storage means comprises a digital tape recorder.

7. The data acquisition and display apparatus of claim 6 further comprising a monitor means for viewing graphics data, the monitor means being coupled to the graphics output.

8. The data acquisition and display apparatus of claim 7 further comprising a means for converting data to a video format, the video format means being coupled to the graphics output.

9. The data acquisition and display apparatus of claim 8 wherein the ultrasonic scanning head means further comprises a reticulated ultrasound array.

10. The data acquisition and display apparatus of claim 4 wherein the transducer comprises a piezoelectric transducer.

11. The data acquisition and display apparatus of claim 1 wherein the ultrasonic scanning head means further comprises a reticulated ultrasound array.

12. The data acquisition and display apparatus of claim 1 wherein the first digital signal processing means includes a digital tape output, the data acquisition and display apparatus further comprising a digital storage means for storing data coupled to the digital tape output.

13. The data acquisition and display apparatus of claim 12 wherein the digital storage means comprises a digital tape recorder.

14. An ultrasound camera comprising:

(a) processing electronics contained in a box;

(b) an array of piezoelectric transducers mounted and contained in the box and connected to the processing electronics via a printed circuit board mount;

(c) a source following circuit mounted and contained in the box, wherein each transducer in the array of piezoelectric transducers is coupled to the source following circuit, comprising a first diode connected between an output of each transducer and an integrated circuit substrate, wherein the source following circuit also includes a source following transistor connected at a gate to the output of each transducer, and wherein the source following transistor is connected at its emitter to a multiplexer, and wherein the source following transistor is connected at its source to the integrated circuit substrate; and (d) a thin cable attached through the box and to graphics processing apparatus, connected to a remote computer processor.

15. An ultrasonic input circuit comprising:

(a) a transducer having a diode connected across a bias voltage, wherein the bias voltage is connected to one terminal of the transducer and the diode is connected to a second terminal of the transducer;

(b) a current source connected between the bias voltage and an emitter of a preamplifier wherein a gate of the preamplifier is connected to the second terminal of the transducer; and (c) a reference voltage supply connected to a drain of the preamplifier, wherein the preamplifier is switched under control of a digital controller wherein the digital controller can sample at least one time period of an output of the preamplifier source into at least one integration capacitor.

16. The ultrasonic input circuit of claim 15 wherein the transducer comprises a piezoelectric transducer.

17. The ultrasonic input circuit of claim 15 further comprising a multiplexer coupled to read out a signal stored by the integration capacitor.

18. The ultrasonic input circuit of claim 15 wherein the digital controller comprises a shift register.

19. The ultrasonic input circuit of claim 15 wherein the digital controller is coupled to a plurality of storage elements for individually sampling an output of the preamplifier source at periodic intervals.

* * * * *

UNITED STATES PATENT AND TRADEMARK OFFICE
CERTIFICATE OF CORRECTION

PATENT NO. : 5,483,963
DATED : January 16, 1996
INVENTOR(S) : Butler et al.

It is certified that error appears in the above-identified patent and that said Letters Patent is hereby corrected as shown below:

Column 6, line 26, delete the word "embodizent" and replace it with
-- embodiment --.

Signed and Sealed this

Eighth Day of December, 1998

*Attest:*

BRUCE LEHMAN

*Attesting Officer*   Commissioner of Patents and Trademarks